United States Patent
Peine

(10) Patent No.: US 11,090,126 B2
(45) Date of Patent: Aug. 17, 2021

(54) INPUT DEVICE HANDLE FOR ROBOTIC SURGICAL SYSTEMS CAPABLE OF LARGE ROTATIONS ABOUT A ROLL AXIS

(71) Applicant: Covidien LP, Mansfield, MA (US)

(72) Inventor: William Peine, Ashland, MA (US)

(73) Assignee: COVIDIEN LP, Mansfield, MA (US)

( * ) Notice: Subject to any disclaimer, the term of this patent is extended or adjusted under 35 U.S.C. 154(b) by 208 days.

(21) Appl. No.: 16/081,728

(22) PCT Filed: Mar. 2, 2017

(86) PCT No.: PCT/US2017/020341
§ 371 (c)(1),
(2) Date: Aug. 31, 2018

(87) PCT Pub. No.: WO2017/151850
PCT Pub. Date: Sep. 8, 2017

(65) Prior Publication Data
US 2019/0090971 A1    Mar. 28, 2019

Related U.S. Application Data

(60) Provisional application No. 62/302,866, filed on Mar. 3, 2016.

(51) Int. Cl.
*A61B 34/00*    (2016.01)
(52) U.S. Cl.
CPC .................................. *A61B 34/74* (2016.02)
(58) Field of Classification Search
CPC ......... A61B 34/30; A61B 34/35; A61B 34/37; A61B 34/70; A61B 34/74; A61B 2034/301; A61B 2034/302; A61B 2034/303; A61B 34/76; A61B 34/77
See application file for complete search history.

(56) References Cited

U.S. PATENT DOCUMENTS

| | | |
|---|---|---|
| 8,828,023 B2 | 9/2014 | Neff et al. |
| 10,335,183 B2 | 7/2019 | Worrell et al. |
| 2010/0228265 A1 | 9/2010 | Prisco |
| 2012/0265176 A1 | 10/2012 | Braun |
| 2013/0296982 A1 | 11/2013 | Feng et al. |
| 2014/0005682 A1* | 1/2014 | Worrell .......... A61B 17/320092 606/130 |
| 2014/0194897 A1 | 7/2014 | Kirschenman et al. |
| 2015/0080880 A1 | 3/2015 | Sartor et al. |

(Continued)

FOREIGN PATENT DOCUMENTS

| | | |
|---|---|---|
| WO | 2016015233 A1 | 2/2016 |
| WO | 2017151850 A1 | 9/2017 |

OTHER PUBLICATIONS

International Search Report dated Jun. 9, 2017 issued in PCT/US2017/020341.

(Continued)

*Primary Examiner* — Melanie R Tyson

(57) ABSTRACT

An input device handle for controlling a robotic system includes a body and a cylinder. The body defines an opening that rotatably receives the cylinder. The cylinder defines a roll axis such that rotation of the cylinder relative to the body about the roll axis is configured to rotate a tool of a robot about a first axis defined by the tool.

9 Claims, 4 Drawing Sheets

(56) References Cited

U.S. PATENT DOCUMENTS

2015/0088122 A1    3/2015  Jensen

OTHER PUBLICATIONS

European Search Report dated Sep. 19, 2019, issued in EP Appln. No. 17760768.
Chinese First Office Action dated Sep. 30, 2020 corresponding to counterpart Patent Application CN 201780012326.8.
Chinese Second Office Action dated Mar. 18, 2021 corresponding to counterpart Patent Application CN 201780012326.8.

* cited by examiner

INPUT DEVICE HANDLE FOR ROBOTIC SURGICAL SYSTEMS CAPABLE OF LARGE ROTATIONS ABOUT A ROLL AXIS

CROSS-REFERENCE TO RELATED APPLICATIONS

This application is a U.S. National Stage Application filed under 35 U.S.C. § 371(a) of International patent Application Serial No. PCT/US2017/020341, filed Mar. 2, 2017, which claims the benefit of and priority to U.S. Provisional patent Application Ser. No. 62/302,866, filed Mar. 3, 2016, the entire disclosure of which is incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector that acts on a patient. The user interface includes an input controller or handle that is moveable by the surgeon to control the robotic surgical system.

Robotic surgical systems typically used a scaling factor to scale down the motions of the surgeon's hands to determine the desired position of the end effector within the patient so that the surgeon could more precisely move the end effector inside the patient. However, the larger the scaling factor, the farther the surgeon had to move the input device handle to move the end effector the same distance. Since the input device handle has a fixed range of motion, this meant that for larger scaling factors the surgeon may have reached an end of the range of motion of an input handle more often.

In addition, during a medical procedure a surgeon may need to rotate the end effector about a roll axis. For example, during a suturing procedure, large rotations of an end effector may be required. Such large rotations typically require multiple clutching events of an input device handle or unnatural rotations of the input device handle.

There is a need for an input device handle for a robotic surgical system that is able to handle large rotations about the roll axis.

SUMMARY

This disclosure generally relates to an input device handle including a body and a cylinder that is rotatable relative to the body. Rotation of the cylinder is configured to affect rotation of the tool such that the tool can be rotating without rolling of the arm of the clinician. By allowing the tool to be rotated without rolling the arm of the clinician, the tool can be continuously rolled without clutching of the user interface or being limited by anatomical limits of the clinician.

In an aspect of the present disclosure, an input device handle for controlling a robot includes a body and a cylinder. The body defines an opening that rotatably receives the cylinder. The cylinder defines a roll axis such that rotation of the cylinder relative to the body about the roll axis is configured to rotate a tool of the robot about a first axis that is defined by the tool. The rotation of the cylinder about the roll axis may be scaled to rotation of the tool about the first axis.

In aspects, the cylinder frictionally engages the body such that as the body is rotated about the roll axis, the cylinder is rotated about the roll axis. Rotation of the body about the roll axis may be configured to rotate the tool of the robot about the first axis. Alternatively, rotation of the body about the roll axis may be configured to rotate a shaft supporting the tool about a second axis that is defined by the shaft. The first and second axis may be coincident with one another.

In some aspects, the body may include a connection portion that defines the opening. The connection portion may be configured to couple to an input shaft of a gimbal of a user interface.

In certain aspects, the input device handle includes an actuation control that is pivotally coupled to the body and that is configured to actuate jaws of the tool. The body may include a button that is configured to control a function of the tool.

In particular aspects, the cylinder includes an engagement feature. The engagement feature may be alternating ribs and recesses. Additionally or alternatively, the engagement feature may be a textured surface.

In another aspect of the present disclosure, a robotic system includes a robot and a user interface. The robot includes an arm and a tool that is support at the end of the arm. The tool defines a first axis. The user interface is in operable communication with the robot to control the tool. The user interface includes a control arm, a gimbal, and an input shaft. The gimbal is supported by the control arm and has an input shaft. The input device handle is coupled to the input shaft and defines a roll axis. The input device handle includes a body and a cylinder. The body defines an opening that rotatably receives the cylinder. The cylinder is disposed within the opening defined in the body and is rotatable about a roll axis such that rotation of the cylinder relative to the body about the roll axis rotates the tool about the first axis.

In aspects, rotation of the cylinder about the roll axis rotates the tool about the first axis. Rotation of the body about the roll axis may rotate the tool about the first axis.

In some aspects, the robot includes a shaft that supports the tool and defines a second axis. Rotation of the body about the tool axis may rotate the shaft about the second axis.

In particular aspects, the gimbal includes a first sensor that is configured to detect rotation of the input shaft relative to the gimbal. The first sensor can be disposed within the input shaft. The input device handle can include a second sensor that is configured to detect rotation of the cylinder relative to the body.

In another aspect of the present disclosure, a method of manipulating a tool of a robot using an input device handle of a user interface includes rotating a cylinder of the input device handle relative to a body of the input device handle about a roll axis that is defined by an input shaft of the user interface to rotate a tool of the robot about a first axis which is defined by the tool.

In aspects, the method further includes rotating the body about the roll axis to rotate the tool about the first axis. The method may include rotating the body about the roll axis to rotate a shaft that supports the tool about a second axis defined by the shaft. The method may include articulating the tool relative to the shaft before rotating the cylinder. Articulating the tool relative to the shaft may include articulating the first axis relative to the second axis.

Further details and aspects of exemplary embodiments of the present disclosure are described in more detail below with reference to the appended figures.

BRIEF DESCRIPTION OF THE DRAWINGS

Various aspects of the present disclosure are described herein below with reference to the drawings, which are incorporated in and constitute a part of this specification, wherein.

DETAILED DESCRIPTION

Figure 1:
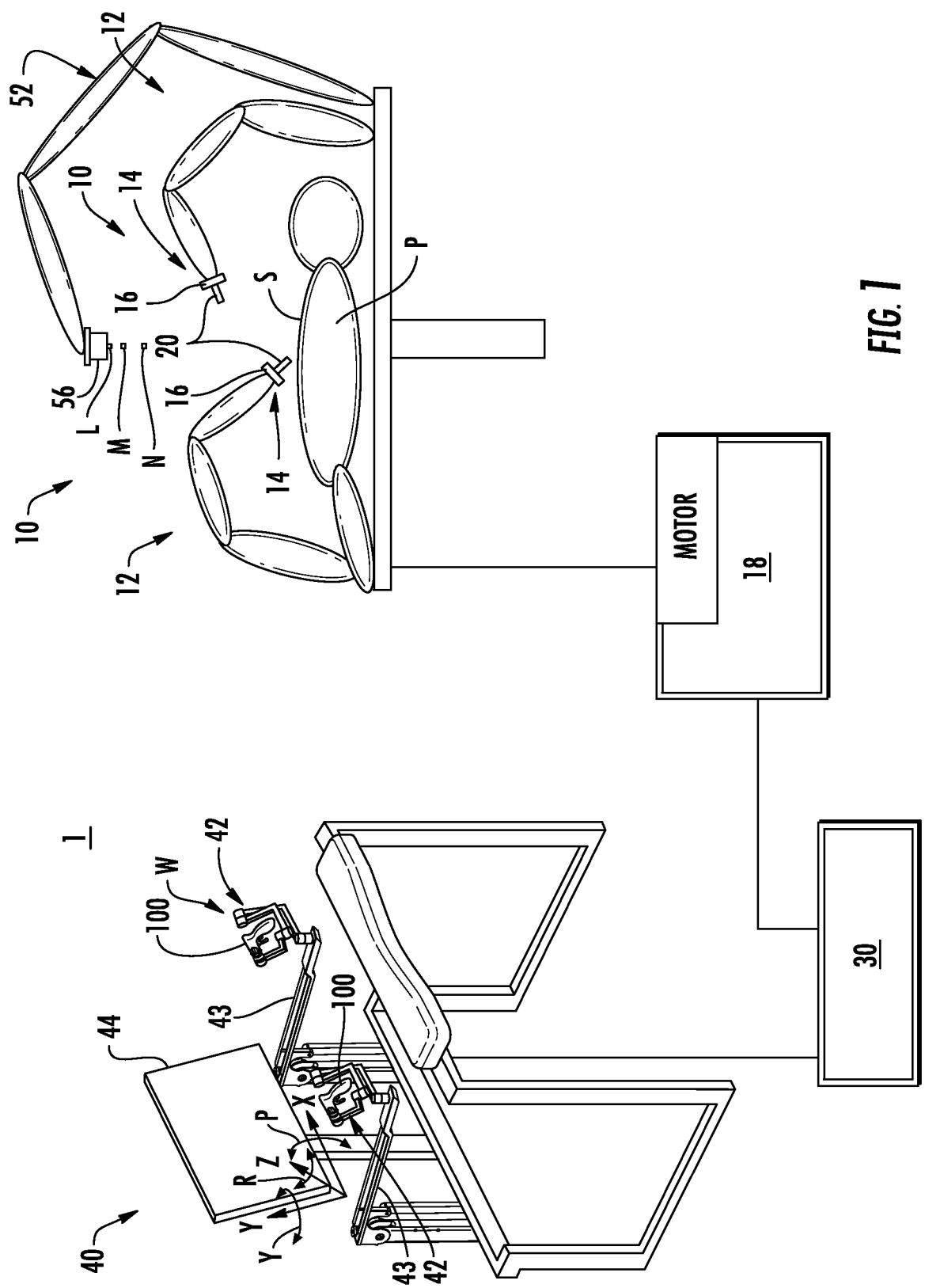
FIG. 1 is a schematic illustration of a user interface and a robotic system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician. In addition, as used herein the term "neutral" is understood to mean non-scaled.

This disclosure generally relates to an input device handle for use with a user interface to control a robotic system. The input device handle includes a rotation control that is associated with one or more roll axes of a tool of the robotic system. The rotation control includes a cylinder capable of rotation about a roll axis of a gimbal of the user interface relative to a body of the input device handle. The cylinder may be associated with rotation of the tool about a tool axis defined between jaws of the tool. In addition, rotation of the body of the input device handle about the roll axis of the gimbal may be associated with rotation about the tool axis. Alternatively, the tool may be articulated relative to a shaft supporting the tool and rotation of the body of the input device handle about the roll axis of the gimbal may be associated with rotation about a shaft axis defined by the shaft.

Referring to FIG. 1, a robotic surgical system 1 in accordance with the present disclosure is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of arms each having an end 14 that supports an end effector or tool 20 which is configured to act on tissue. In addition, the ends 14 of the arms 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the arms 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes gimbals 42 which are supported on control arms 43 which allow a clinician to manipulate the robotic system 10 (e.g., move the arms 12, the ends 14 of the arms 12, and/or the tools 20). Each of the gimbals 42 is in communication with the processing unit 30 to transmit control signals thereto and to receive feedback signals therefrom. Additionally or alternatively, each of the gimbals 42 may include input devices handles 100 (FIG. 2) which allow the surgeon to manipulate (e.g., clamp, grasp, fire, open, close, rotate, thrust, slice, etc.) the tools 20 supported at the ends 14 of the arms 12.

Figure 2:
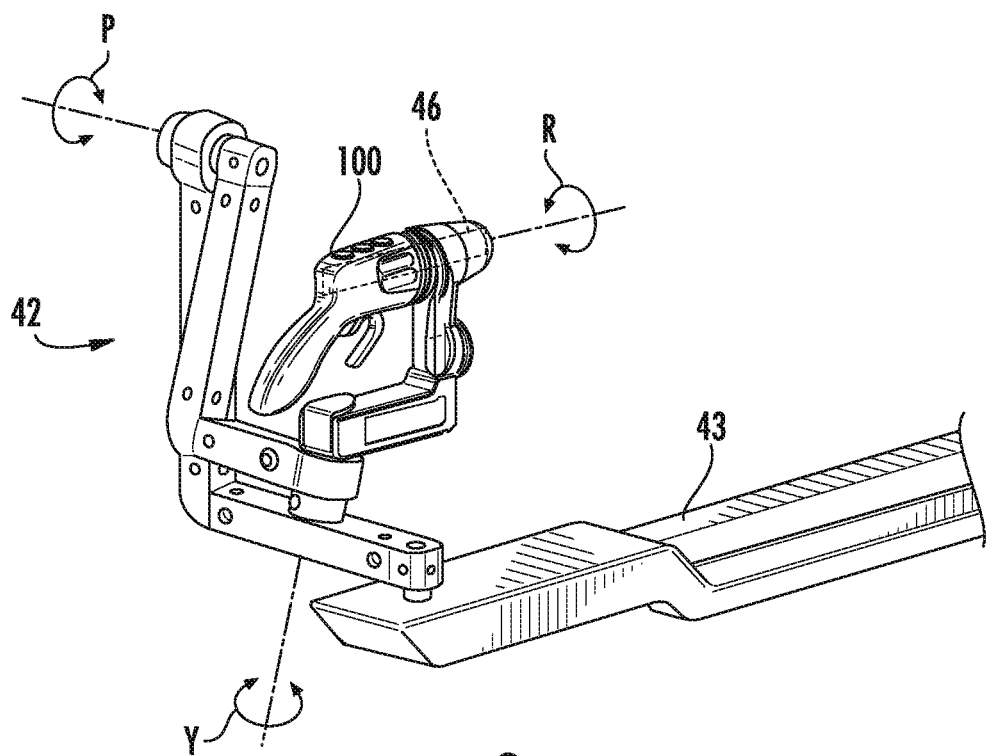
FIG. 2 is a perspective view of a input device handle supported on an end of a control arm of the user interface of FIG. 1.

With additional reference to FIG. 2, each of the input devices handles 100 is moveable through a predefined workspace to move the ends 14 of the arms 12 within a surgical site "S". The three-dimensional images on the display device 44 are orientated such that the movement of the input handle 42, as a result of the movement of the input device handles 100, moves the ends 14 of the arms 12 as viewed on the display device 44. It will be appreciated that the orientation of the three-dimensional images on the display device 44 may be mirrored or rotated relative to view from above the patient "P". In addition, it will be appreciated that the size of the three-dimensional images on the display device 44 may be scaled to be larger or smaller than the actual structures of the surgical site permitting a clinician to have a better view of structures within the surgical site "S". As the input devices handles 100 are moved, the tools 20 are moved within the surgical site "S" as detailed below. As detailed herein, movement of the tools 20 may also include movement of the ends 14 of the arms 12 which support the tools 20.

For a detailed discussion of the construction and operation of a robotic surgical system 1, reference may be made to U.S. Pat. No. 8,828,023, the entire contents of which are incorporated herein by reference.

Figure 3:
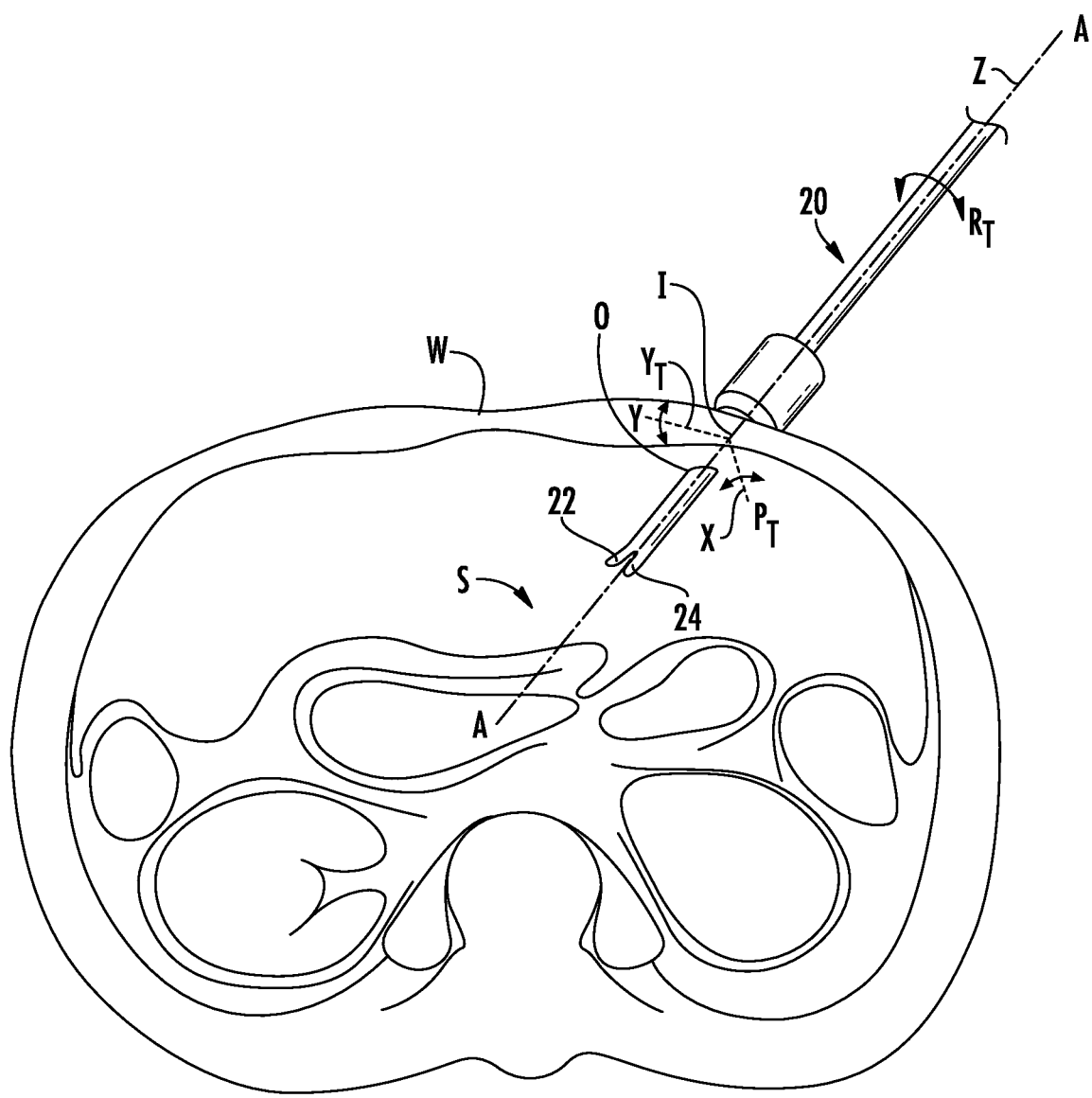
FIG. 3 is a cutaway view of a body cavity of a patient showing a tool of the robotic surgical system of FIG. 1 inserted in the body cavity.

Referring to FIGS. 2 and 3, the input device handle 100 is supported on a connection arm 46 of the gimbal 42. The connection arm 46 defines a roll axis "R" of the user interface 40. It will be appreciated that rotation of the connection arm 46 about the roll axis "R" rotates the tool 20 about tool roll axis "RT" as shown in FIG. 3.

Figure 4:
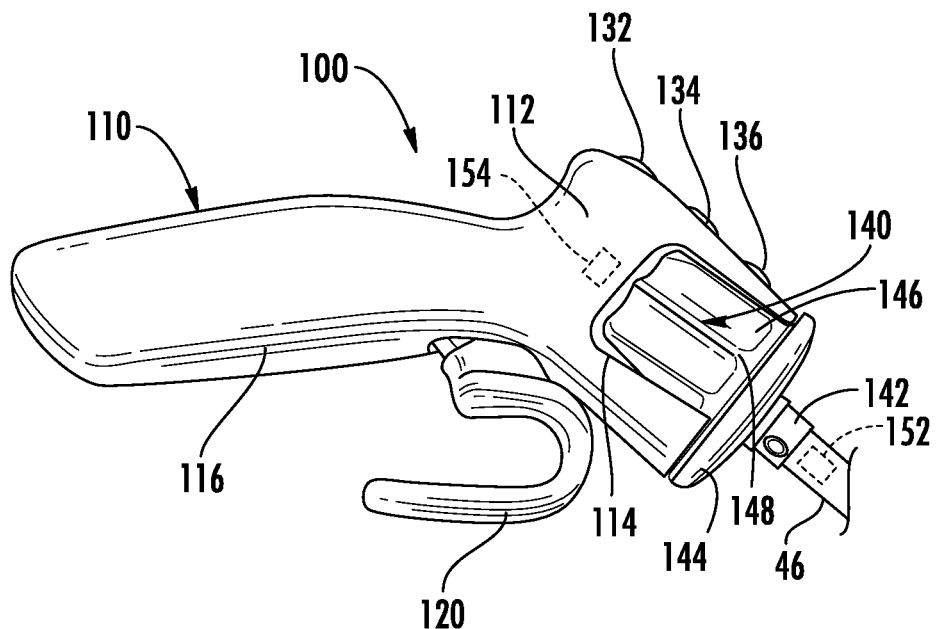
FIG. 4 is a side perspective view of the input device handle of FIG. 2.

With reference to FIG. 4, the input device handle 100 in accordance with the present disclosure includes a body 110, an actuation control 120, one or more control buttons 132-136, and a rotation control 140. The body 110 includes a connection portion 112 and a handle 116 extending proximally from the connection portion 112. The connection portion 112 that defines an opening 114 which rotatably receives the rotation control 140. The actuation control 120 may be in the form of a trigger that is pivotally coupled to the body 110. Pivoting the actuation control 120 between a first position and a second position may actuate jaws 22, 24 (FIG. 3) of the tool 20 between a first or open configuration and a second or closed configuration. The buttons 132-136 are in operable communication with the processing unit 30 (FIG. 1) to selectively control functions of the tool 20. For example, button 132 may fix the configuration of the jaws 22, 24 relative to one another, button 134 may fire a fastener (not shown) from one of jaws 22, 24, and button 136 may actuate a knife (not shown) through the jaws 22, 24. Additionally or alternatively, one of the buttons 132-136 may activate a source of electrosurgical energy such that electrosurgical energy is delivered to tissue via the tool 20.

The rotation control 140 includes a coupling neck 142, an end cap 144, and a cylinder 146. The coupling neck 142 is disposed about the connection arm 46 of the gimbal 42 to couple the input device handle 100 to the connection arm 46. The coupling neck 142 is rotatably fixed to the connection arm 46 and the cylinder 146 such that rotation of the cylinder 146 rotates the connection arm 46 about the roll axis "R" of the gimbal 42. The cylinder 146 is rotatably disposed within the opening 114 of the body 110 such that the cylinder 146 may be rotated relative to the body 110. The cylinder 146 may be frictionally engaged with the body 110 such that the cylinder 146 rotates with the body 110 in response to the body 110 being rotated about the roll axis "R" of the gimbal 42. The cylinder 146 may include engagement features 148 that are engagable by a clinician to rotate the cylinder 146 relative to the body 110. It is envisioned that the cylinder 146 may be engaged by the thumb of a clinician gripping the handle 114. The engagement features 148 may be alternating ribs and recesses as shown in FIG. 4. Additionally or alternatively, the engagement features 148 may include a textured surface or any known surface or feature that enhances engagement of a finger of a clinician with the cylinder 146.

Rotation of the cylinder 146 is measured by a rotation sensor, such as a rotary encoder 152, in the connection arm 46 supporting the input device handle 100. It is envisioned that the rotary encoder 152 can be disposed within the connection arm 46 and/or within the gimbal 42 to detect rotation of the connection arm 46 about the roll axis "R". In addition, the rotational position of the cylinder 146 relative to the input device handle 100 could also be measured using a second sensor or encoder 154 in the body 110, which may allow improved gravity compensation of the input device handle 100 and other more advanced control functions. As described above, rotation of the cylinder 146 can be accomplished by rotating the entire input device handle 100 and allowing the friction between the cylinder 146 and the input device handle 100 to rotate the cylinder 146, or the input device handle 100 can be held fixed and the cylinder 146 can be rotated relative to the input device handle 100 by a thumb of a clinician. In both cases, rotation of the cylinder 146 about the roll axis "R" of the gimbal 42 is measured and is used to control rolling motion of the instrument 20.

By providing a cylinder 146 that is rotatable relative to the body 110 of the input device handle 100, the dexterity of the clinician can be increased by allowing large rotations of the tool 20 about the tool roll axis "RT" (FIG. 5) with minimal or no rotation of the handle 116 about the roll axis "R" of the gimbal 42.

Figure 5:
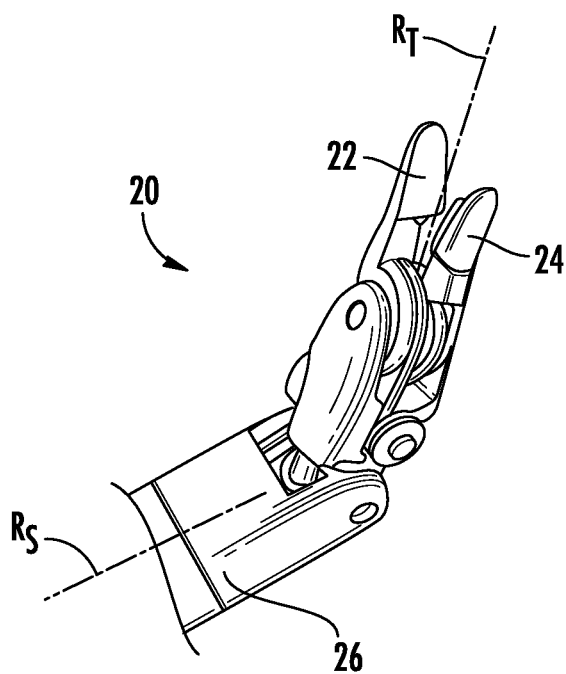
FIG. 5 is a perspective view of the tool of FIG. 3.

With additional reference to FIG. 5, a tool 20 may include first and second jaws 22, 24 that are pivotally supported at an end of a tool shaft 26. The first and second jaws 22, 24 define the tool roll axis "RT" that passes through a center line between the first and second jaws 22, 24 and the tool shaft 26 defines a shaft roll axis "Rs". In such embodiments, rotation of the cylinder 146 and/or the handle 116 about the roll axis "R" of the gimbal 42, rotates the first and second jaws 22, 24 about the tool roll axis "RT". Alternatively, rotation of the cylinder 146 about the roll axis "R" of the gimbal 42 may rotate the first and second jaws 22, 24 about the tool roll axis "RT" and rotation of the handle 116 about the roll axis "R" of the gimbal 42 may rotate the tool 20 about the shaft roll axis "Rs".

It is contemplated that the rotation of the cylinder 146 and/or the handle 116 about the roll axis "R" may be scaled in a positive, neutral, or negative manner to rotation of the tool roll axis "RT" and/or the shaft roll axis "Rs". For a detailed discussion of scaling of rotation reference may be made to U.S. Provisional patent Application Ser. No. 62/265,457, filed Dec. 10, 2015, entitled "ROBOTIC SURGICAL SYSTEMS WITH INDEPENDENT ROLL, PITCH, AND YAW SCALING", the entire contents of which are hereby incorporated by reference.

It will be appreciated that during a surgical procedure that the pitch and yaw motions of the input device handle 100 remain correctly mapped to the tool pitch axis "PT" and the tool yaw axis "YT" as viewed on the display 44. For example, if the clinician rotates the first and second jaws 22, 24 about the tool roll axis "RT" using the cylinder 146, pitching the input device handle 100 down will continue to pitch the tool 20 down relative to the tool pitch axis "PT".

It is envisioned that the cylinder 146 can be used to control functions or features of the system other than rolling the tool 20 about the tool roll axis "RT". For example, the cylinder 146 could be used to roll a camera associated with the cylinder, navigate through a graphical user interface (GUI) on the display 44, actuate a function of the tool 20 (e.g., fire staples from one of the first or second jaw 22, 24), etc.

As detailed above and shown in FIG. 1, the user interface 40 is in operable communication with the robot system 10 to perform a surgical procedure on a patient "P"; however, it is envisioned that the user interface 40 may be in operable communication with a surgical simulator (not shown) to virtually actuate a robot system and/or tool in a simulated environment. For example, the surgical robot system 1 may have a first mode where the user interface 40 is coupled to actuate the robot system 10 and a second mode where the user interface 40 is coupled to the surgical simulator to virtually actuate a robot system. The surgical simulator may be a standalone unit or be integrated into the processing unit 30. The surgical simulator virtually responds to a clinician interfacing with the user interface 40 by providing visual, audible, force, and/or haptic feedback to a clinician through the user interface 40. For example, as a clinician interfaces with the input device handles 100, the surgical simulator moves representative tools that are virtually acting on tissue at a simulated surgical site. It is envisioned that the surgical simulator may allow a clinician to practice a surgical procedure before performing the surgical procedure on a patient. In addition, the surgical simulator may be used to train a clinician on a surgical procedure. Further, the surgical simulator may simulate "complications" during a proposed surgical procedure to permit a clinician to plan a surgical procedure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An input device handle for controlling a tool of a robot that is physically remote and disconnected from the input device handle, the input device handle comprising:

a body defining an opening; and a cylinder rotatably disposed within the opening and defining a roll axis, wherein rotation of the cylinder relative to the body about the roll axis is configured to rotate the tool of the robot about a first axis defined by the tool of the robot, wherein the roll axis of the cylinder is separated from the longitudinal axis of the tool of the robot, wherein rotation of the body about the roll axis is configured to rotate a shaft pivotally supporting the tool about a second axis defined by the shaft.

2. The input device handle according to claim 1, wherein the cylinder frictionally engages the body such that as the body is rotated about the roll axis, the cylinder is rotated about the roll axis.

3. The input device handle according to claim 1, wherein the body includes a connection portion that defines the opening, the connection portion configured to couple to an input shaft of a gimbal of a user interface.

4. The input device handle according to claim 1, further comprising an actuation control pivotally coupled to the body and configured to actuate jaws of the tool.

5. The input device handle according to claim 1, wherein the body includes a button configured to control a function of the tool.

6. The input device handle according to claim 1, wherein the cylinder includes an engagement feature.

7. The input device handle according to claim 6, wherein the engagement feature is alternating ribs and recesses.

8. The input device handle according to claim 6, wherein the engagement feature is a textured surface.

9. The input device handle according to claim 1, wherein the rotation of the cylinder about the roll axis is scaled to rotation of the tool about the first axis.

* * * * *